(12) United States Patent
Nelson

(10) Patent No.: US 12,213,895 B2
(45) Date of Patent: Feb. 4, 2025

(54) BREAST PROTHESIS

(71) Applicant: Natural Beauty Breast Prosthesis, LLC, Hamilton, NY (US)

(72) Inventor: Jill Alison Nelson, Sherburne, NY (US)

(73) Assignee: Natural Beauty Breast Prosthesis, LLC, Hamilton, NY (US)

( * ) Notice: Subject to any disclaimer, the term of this patent is extended or adjusted under 35 U.S.C. 154(b) by 1065 days.

(21) Appl. No.: 17/074,598

(22) Filed: Oct. 19, 2020

(65) Prior Publication Data
US 2021/0113352 A1    Apr. 22, 2021

Related U.S. Application Data

(60) Provisional application No. 62/923,068, filed on Oct. 18, 2019.

(51) Int. Cl.
*A61F 2/52* (2006.01)
*A41C 3/14* (2006.01)

(52) U.S. Cl.
CPC ............. *A61F 2/52* (2013.01); *A41C 3/148* (2013.01)

(58) Field of Classification Search
CPC ......... A61F 2/52; A41C 3/148; A41C 3/0064; A41C 3/0071; A41C 3/0092; A41C 3/04; A41C 3/10
See application file for complete search history.

(56) References Cited

U.S. PATENT DOCUMENTS

| | | | | |
|---|---|---|---|---|
| 1,365,731 A | * | 1/1921 | Schloss | A41F 17/00 2/273 |
| 5,071,433 A | * | 12/1991 | Naestoft | A61F 2/52 450/55 |
| 6,156,065 A | * | 12/2000 | Eaton | A41C 3/0071 450/55 |

FOREIGN PATENT DOCUMENTS

| | | | | |
|---|---|---|---|---|
| CN | 105455210 A | * | 4/2016 | A41C 3/12 |
| TW | 513591 U | * | 12/2015 | |

OTHER PUBLICATIONS

CN-105455210-A_Translation (Year: 2016).*
TW-513591-U_Translation (Year: 2015).*

* cited by examiner

*Primary Examiner* — Brian A Dukert
*Assistant Examiner* — Rebecca Lynee Zimmerman
(74) *Attorney, Agent, or Firm* — Vedder Price P.C.

(57) ABSTRACT

Embodiments comprise a breast prosthesis. The prosthesis includes a body and a set of straps. In some embodiments, the body is comprised of a cover, on which the straps are disposed, and internal components. The straps connect the body to the person's undergarment in such a way that doesn't need sewing to the undergarment itself. The straps also hold the prosthesis in place, such that it doesn't shift or move, or does so very minimally. A person can use their own bra or similar garment of their choosing, instead of having to purchase a special mastectomy bra.

19 Claims, 18 Drawing Sheets

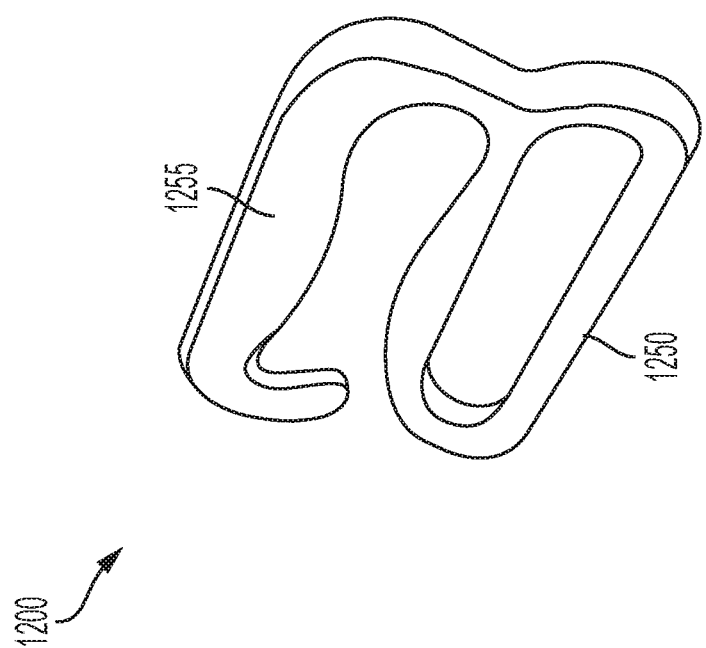

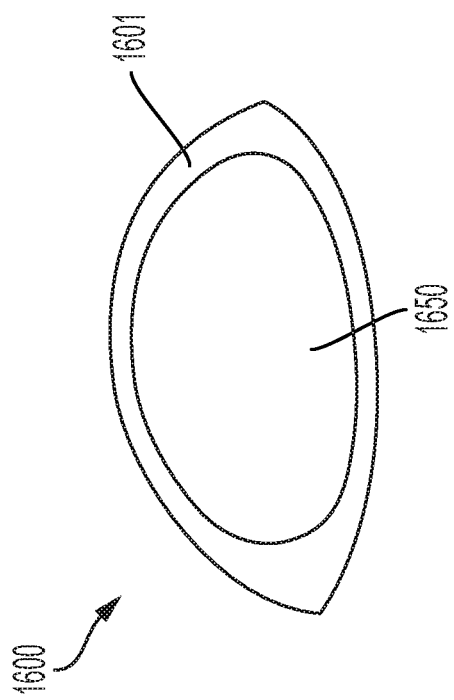

BREAST PROTHESIS

PRIORITY CLAIM

The present patent document is a continuation of U.S. patent application Ser. No. 62/923,068, filed Oct. 18, 2019, entitled "BREAST PROSTHESIS", the entire disclosure of which is incorporated herein by reference.

FIELD OF THE INVENTION

Embodiments of the invention include a breast prosthesis that can be attached to a conventional brazier (bra).

BACKGROUND

As part of a breast cancer treatment, or for other medical purposes, a person may have one or more breasts removed. Removal of a breast can cause anguish to a person who is not able to look the same as they did prior to the operation. There exists a need for improvements in breast prosthetics to assist people who have had a breast removed.

SUMMARY OF THE INVENTION

Embodiments comprise a breast prosthesis. The prosthesis includes a body and a set of straps. In some embodiments, the body is comprised of a cover, on which the straps are disposed, and internal components. The straps connect the body to the person's undergarment in such a way that doesn't need sewing to the undergarment itself. The straps also hold the prosthesis in place, such that it doesn't shift or move, or does so very minimally. A person can use their own bra or similar garment of their choosing, instead of having to purchase a special mastectomy bra.

In some embodiments, there is provided a breast prosthesis including a cover and at least one internal component, wherein the cover has a hollow interior; a first strap; an attachment point for the first strap; a second strap having a first portion that extends from an exterior of the cover, wherein the first portion of the second strap has a first magnet therein; and a third strap having a first portion that extends from the exterior of the cover of the prothesis, wherein the first portion of the third strap has a second magnet therein; and wherein the at least one internal component includes a third magnet and a fourth magnet.

In some embodiments, the first strap is configured to attach around a bra strap, the second strap is configured to wrap over a bra cup and attach via the third magnet attracting the first magnet, and the third strap is configured to wrap over the bra cup and attach via the fourth magnet attracting the second magnet.

In some embodiments, the at least one internal component further includes at least one of a shaper, an insert having a filler, or at least one weight.

In some embodiments, the second strap and the third strap each have a second portion that extends into the interior of the body of the prosthesis. The third magnet is disposed within the second portion of the second strap. The fourth magnet is disposed within the second portion of the third strap.

In some embodiments, the at least one internal component comprises a semi-solid piece.

In some embodiments, the prosthesis and the bra form a system.

BRIEF DESCRIPTION OF THE DRAWINGS

The accompanying drawings, which are incorporated in and constitute a part of this specification, illustrate several embodiments of the present teachings and together with the description, serve to explain the principles of the present teachings. The drawings are not necessarily to scale. The drawings are merely representations, not intended to portray specific parameters of the invention. The drawings are intended to depict only typical embodiments of the invention, and therefore should not be considered as limiting in scope. In the drawings, like numbering represents like elements. Furthermore, certain elements in some of the figures may be omitted, or illustrated not-to-scale, for illustrative clarity.

FIG. 12 shows a hook 1200 in accordance with embodiments.

FIG. 15 shows a cross-section of an example of embodiments including a cover and a filler which is semi-solid.

DETAILED DESCRIPTION OF THE INVENTION

Reference throughout this specification to "one embodiment," "an embodiment," "some embodiments," "in embodiments," or similar language means that a particular feature, structure, or characteristic described in connection with the embodiment is included in at least one embodiment of the present invention. Thus, appearances of the phrases "in one embodiment," "in an embodiment," "in some embodiments," "in embodiments," and similar language throughout this specification may, but do not necessarily, all refer to the same embodiment.

Moreover, the described features, structures, or characteristics of the invention may be combined in any suitable manner in one or more embodiments. It will be apparent to those skilled in the art that various modifications and variations can be made to the present invention without departing from the spirit and scope and purpose of the invention. Thus, it is intended that the present invention cover the modifications and variations of this invention provided they come within the scope of the appended claims and their equivalents. Reference will now be made in detail to the preferred embodiments of the invention.

The terminology used herein is for the purpose of describing particular embodiments only and is not intended to be limiting of this disclosure. As used herein, the singular forms "a", "an", and "the" are intended to include the plural forms as well, unless the context clearly indicates otherwise. Furthermore, the use of the terms "a", "an", etc., do not denote a limitation of quantity, but rather denote the presence of at least one of the referenced items. The term "set" is intended to mean a quantity of at least one. It will be further understood that the terms "comprises" and/or "comprising", or "includes" and/or "including", or "has" and/or "having", when used in this specification, specify the presence of stated features, regions, integers, steps, operations, elements, and/or components, but do not preclude the presence or addition of one or more other features, regions, integers, steps, operations, elements, components, and/or groups thereof.

Embodiments comprise a prosthesis body and a set of straps. In some embodiments, the prosthesis body is comprised of a cover and at least one internal component. The cover may have a hollow interior, so as to fit other components therein. The straps connect the body to the person's undergarment (bra) in such a way that doesn't need sewing to the undergarment itself. The straps also hold the prosthesis in place, such that it doesn't shift or move, or does so very minimally. A person can use their own bra or similar garment of their choosing, instead of having to purchase a special mastectomy bra.

Figure 1B:
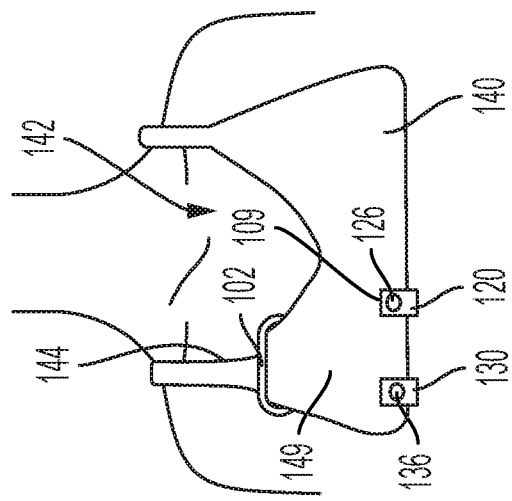
FIG. 1B shows a front view of a bra on a person's body, having the prosthesis of FIG. 1A installed in accordance with embodiments of the invention.
Figure 1A:
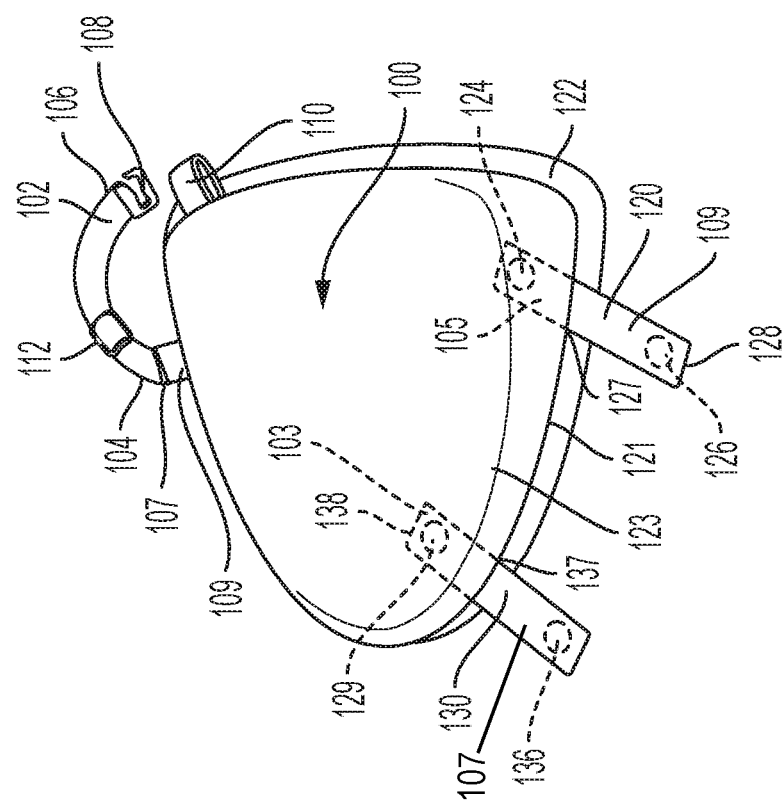
FIG. 1A shows a top-down view of prosthesis body in accordance with embodiments of the present invention.

As shown in FIG. 1A, there is a top-down view of prosthesis body 100. A first strap 102 comprises a soft elongate material having a hook at each end. The elongate material has a first end 104, having a first strap loop, and a second end 106, having a second strap loop. A clasp 107 is attached to the first strap loop, and a hook 108 is attached to the second strap loop. The clasp 107 and hook 108 attach the strap 102 to the prosthesis body 100 by hooking onto body loops 109 and 110, respectively, which are attached to the prosthesis body. Hook 107 may permanently attach to body loop 109, while hook 108 may removably attach to loop 110. Loop 110 is an example of an attachment point for the first strap. In some embodiments, both hooks removably attach. In embodiments, the first strap and the second strap are bendable/flexible. In some embodiments, the cover, straps, and loops may be made from fabric, such as cotton or other suitable material.

In some embodiments, the first strap is adjustable in length. As shown, a slide 112 on strap 102 causes the length of the strap 102 to be adjustable. The adjustability allows a user to customize the tightness of the strap 102 around the bra strap when the prosthesis is applied. Also, the looser the strap 102, the lower it will hang when installed. A user can adjust for the fit they desire.

A second set of straps attached at the lower side of the prosthesis each have two magnets therein. Here, on FIG. 1A, strap 120 and strap 130 are shown in extended position. They may be folded over for use on a bra.

Strap 120 attaches to prosthesis body 100 at seam 121, and is split into two portions by the seam—outer portion 109 (on exterior of the body/cover) and inner portion 105 (inside the interior of the body/cover). The first end of outer portion 109 has one end 127 at seam 121. A second end 128 of strap 102 has magnet 126 embedded/sewn in. Strap portion 103 also has a magnet 124 therein, such that the strap 120 can be folded over the outside of a bra and the magnets 126 and 124 will attract such that the strap 120 (with strap 102 and 130) will hold the bottom of the prosthesis body 100 in place. In some embodiments the first strap portion and the second strap portion are ½ inch to 3 inches long each.

Strap 130 is attached to prosthesis body 100 at seam 121, and is split into two portions by the seam—outer portion 107 (outside/exterior the body/cover) and inner portion 103 (inside the interior of the body/cover). The first end of outer portion 107 has one end 137 at seam 121. Strap portion 107 has magnet 136 embedded/sewn in. The inner portion 103 also has a magnet 129 therein, such that the outer portion 107 of the strap 130 can be folded over the outside of a bra and the magnets 136 and the corresponding magnet 129 in the prosthesis body 100 will attract such that the strap 130 (with straps 120 and 102) will hold the bottom of the prosthesis body 100 in place. In some embodiments the first strap portion and the second strap portion are ½ inch to 3 inches long each.

In some embodiments, instead of straps having an interior portion, the magnets may be sewn into the material of the cover, i.e. disposed within a fabric pocket which is sewn to the interior wall of the cover.

The magnets 124, 126, 129, 136 are of sufficient strength to secure the straps during use. In some embodiments, the magnets 124, 126, 129, 136 may comprise rare-earth magnets. In some embodiments, the magnets 124, 126, 129, 136 are neodymium magnets. In some embodiments, the magnets 124124, 126, 129, 136 are comprised of an alloy of neodymium, iron, and boron ($Nd_2Fe_{14}B$).

FIG. 1B shows a front view of a bra 140 on a person's body 142, having the prosthesis of FIG. 1A installed in accordance with embodiments of the invention. The prosthesis body is between the bra cup 149 and the wearer's breast. Strap 102 is shown around bra strap 144. Straps 120 and 130 are shown on the lower end of the bra 140, folded over such that respective magnets can attract one another. In some embodiments, more or fewer straps with magnets may be included. In some embodiments, straps 120 and 130 are sewn into a seam 121 of two pieces of soft walls 123, 122 of the cover. In some embodiments, loops 109 and 110 are sewn into a seam 121 of two pieces of wals 123, 122 that form the cover. As shown in FIG. 1B, in some embodiments, the prosthesis and bra together form a system.

Figure 1C:
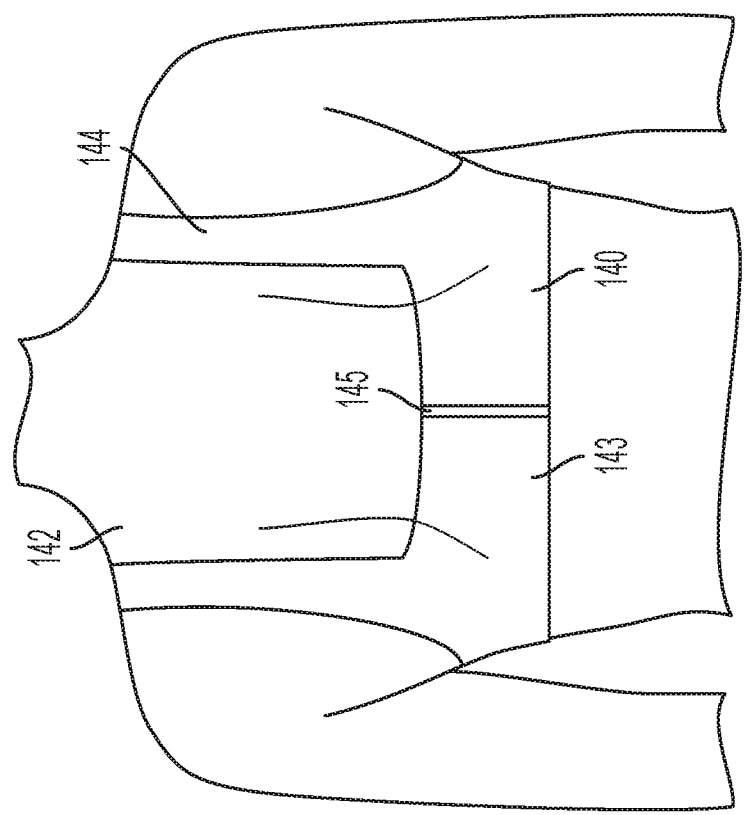
FIG. 1C shows a front view of a bra on a person's body, having the prosthesis of FIG. 1A installed (not in view) in accordance with embodiments of the invention.

FIG. 1C shows a back view of a bra 140 on a person's body 142, having the prosthesis of FIG. 1A installed (not in view) in accordance with embodiments of the invention. In some embodiments, the bra 140 has a back band 143 and a clasp 145. Clasp may be any standard bra clasp. In some embodiments, clasp 145 is not present, and instead, the backband is a single piece of fabric, such as a sports bra. The bra 140 may be any bra the user chooses. Embodiments provide the freedom to the user to select a bra, rather than having to use a special mastectomy bra.

Accordingly, in some embodiments, there is provided a breast prosthesis including a cover and at least one internal component, wherein the cover has a hollow interior; a first strap; an attachment point for the first strap; a second strap having a first portion that extends from an exterior of the cover, wherein the first portion of the second strap has a first magnet therein; and a third strap having a first portion that extends from the exterior of the cover of the prothesis, wherein the first portion of the third strap has a second magnet therein; and wherein the at least one internal component includes a third magnet and a fourth magnet.

In some embodiments, the second strap and the third strap each have a second portion that extends into the interior of the body of the prosthesis. The third magnet is disposed within the second portion of the second strap. The fourth magnet is disposed within the second portion of the third strap.

Figure 2:
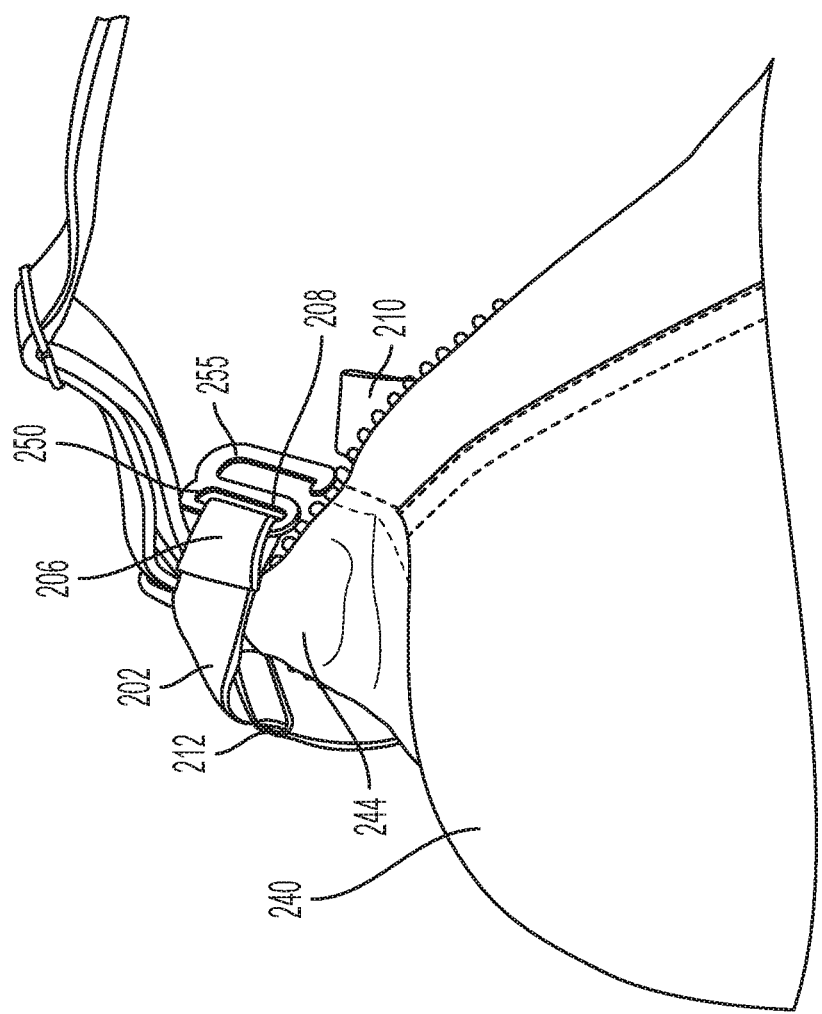
FIG. 2 shows a portion of a bra having a prosthesis thereunder.

FIG. 2 shows a bra 240 (partial view shown) having a prosthesis of embodiments thereunder. Hook 208 is in view, similar to hook 108. This hook is removably attachable to a loop 210 (similar to 110) on the prosthesis body. Hook 208 has closed loop 250 and open loop 255. Closed loop 250 attaches the hook 208 to the strap loop 206. Open loop 255 removably attaches to body loop 210. The strap 202 is shown around bra strap 244. Slide 212 is shown. Note that straps 220, 230, and 202 are substantially similar to straps 102, 120 and 130, including their configuration.

Figure 3:
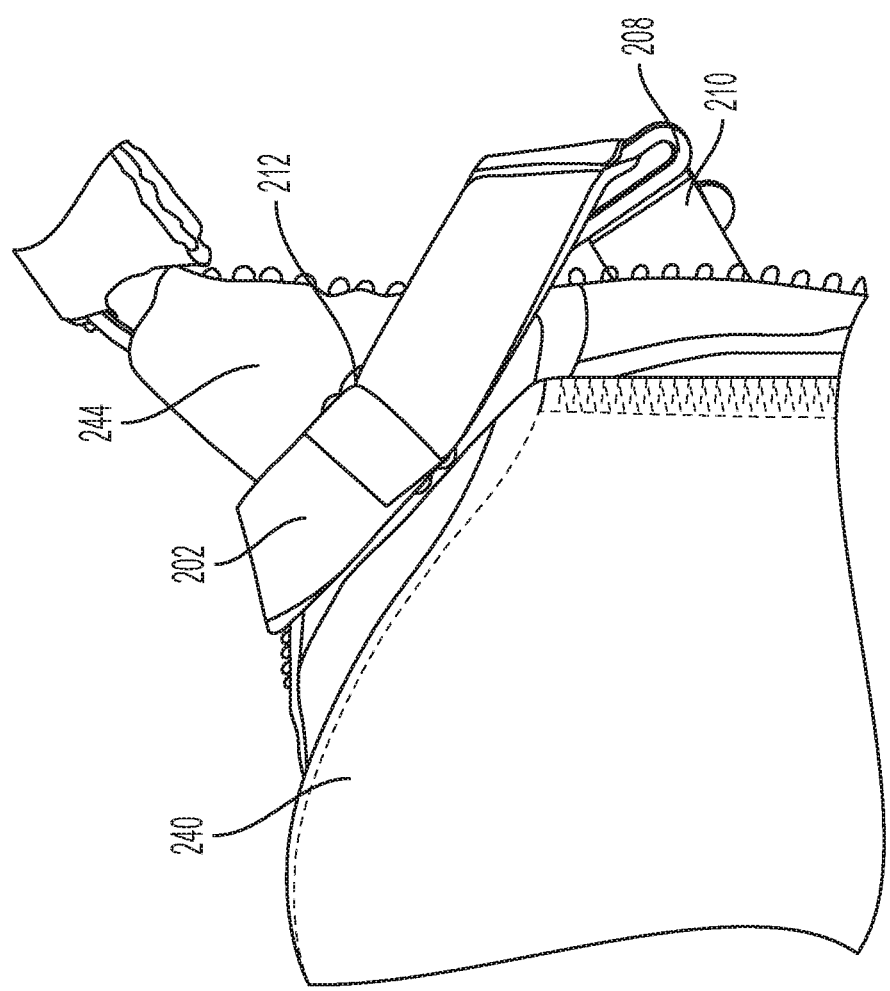
FIG. 3 shows the prosthesis strap around a bra strap of bra.

FIG. 3 shows the strap 202 around a bra strap 244 of bra 240 (partial view shown). Hook 208 is shown attached too body loop 210. Strap 202 is turned over so as the underside of slide 212 is in view.

Figure 4:
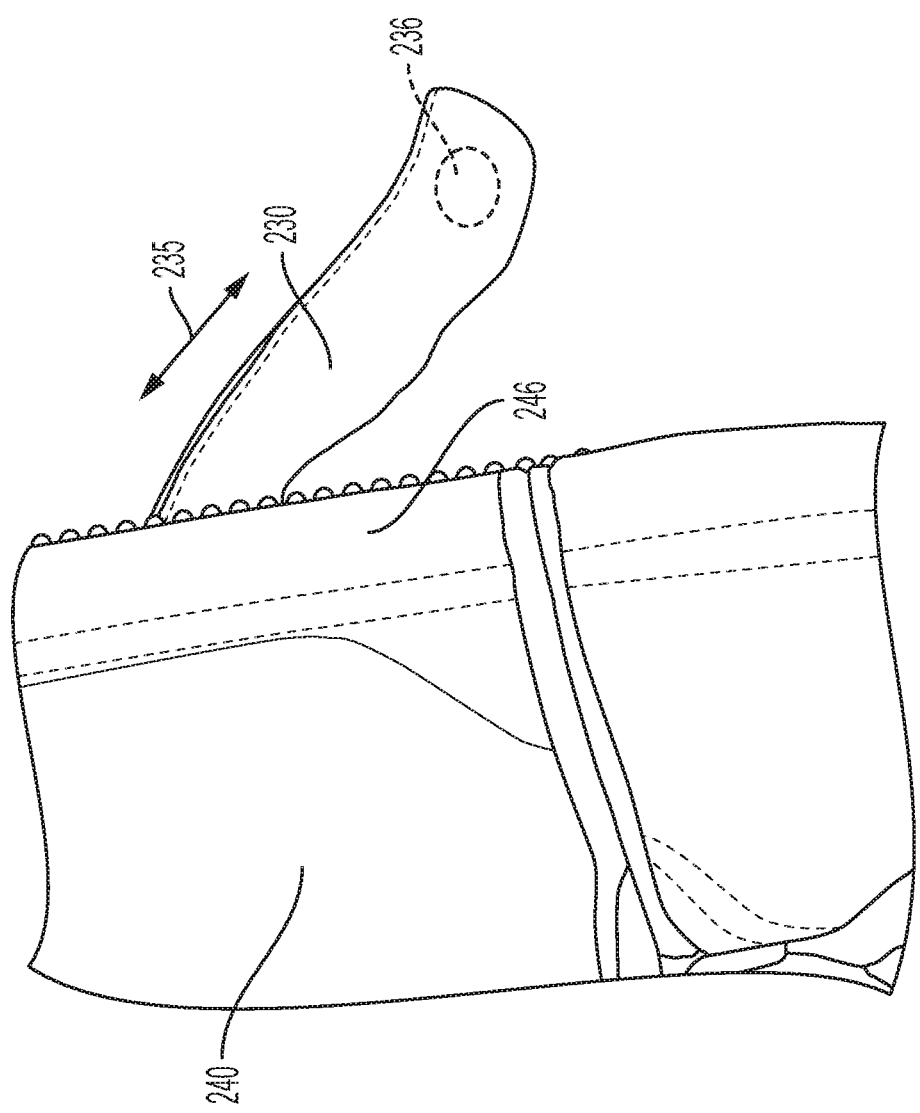
FIG. 4 shows a top-down view of the prosthesis strap in extended position over a bra.

FIG. 4 shows a top-down view of (outer portion of) strap 230 in extended position over a bra 240 (partial view shown). Magnet 236 is sewn into strap 230. Interior of the strap 230 is hollow, so a user can push the magnet 236 in the directions indicated by the arrow 235, interiorly, to adjust the magnet placement according to the width of the front bra band 246 (the lower side of the bra when oriented on a person) that the strap 230 must fold over to align the magnet 236 with a magnet inside the prosthesis body, in some embodiments, in a (inner portion of) strap 230. Strap 220 is similar.

Note that the bra shown in FIG. 4 and in other images is an example, and that any suitable bra can be used. In some embodiments, a bra and the prosthesis are a set.

Figure 5:
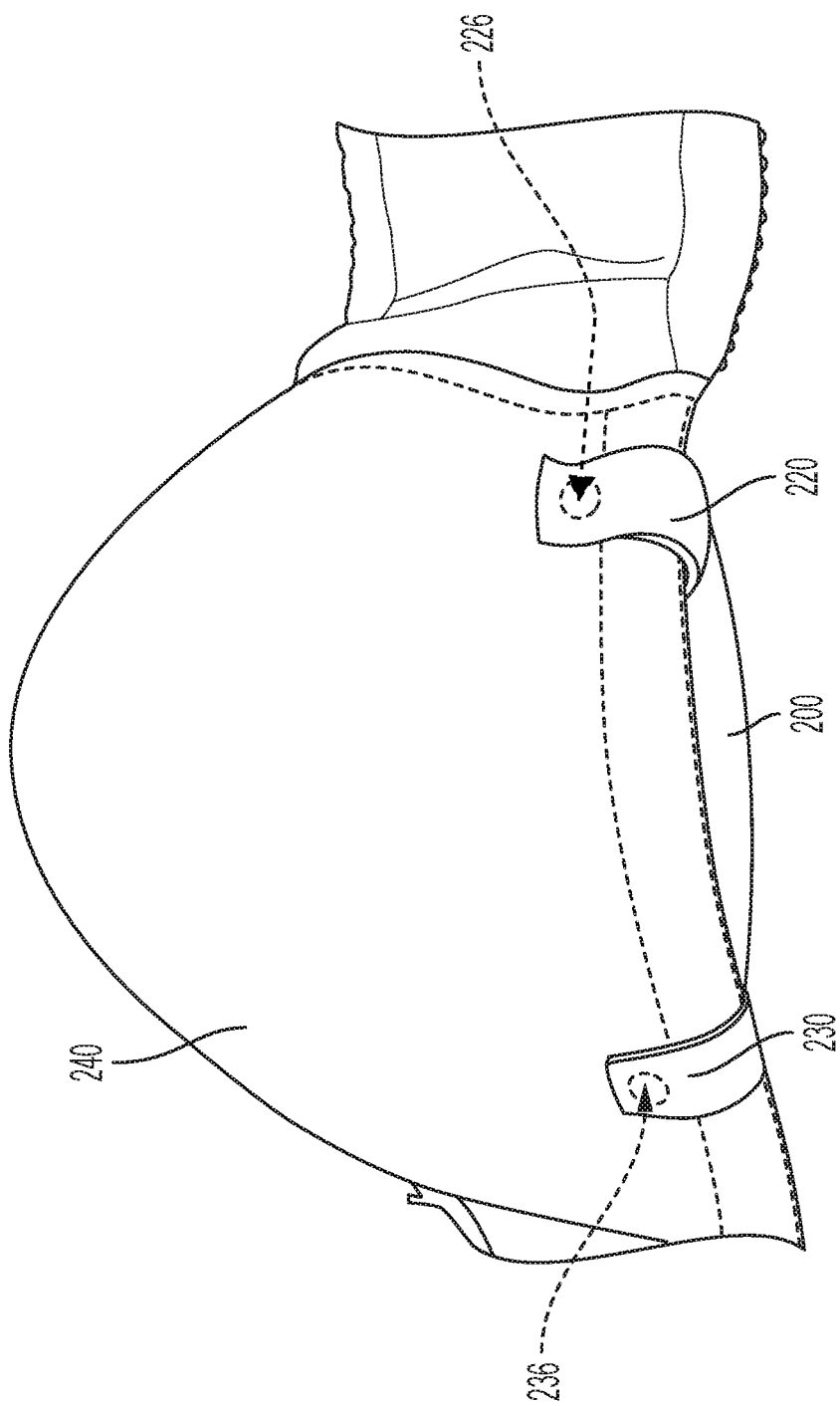
FIG. 5 shows a partial view of the prosthesis attached from below on the right side of bra.

FIG. 5 shows partial view of the prosthesis attached from below to the right side of bra 240 (whereas in FIG. 1B, it was attached to the left side when viewed facing body 142 of a wearer). Prosthesis body 200 is in view under bra 240. Straps 220 and 230 (outer portions thereof) are folded over such that magnets 226, and 236, respectively can attract magnets attached to the inner portions of the straps inside the prosthesis body 200.

Figure 6:
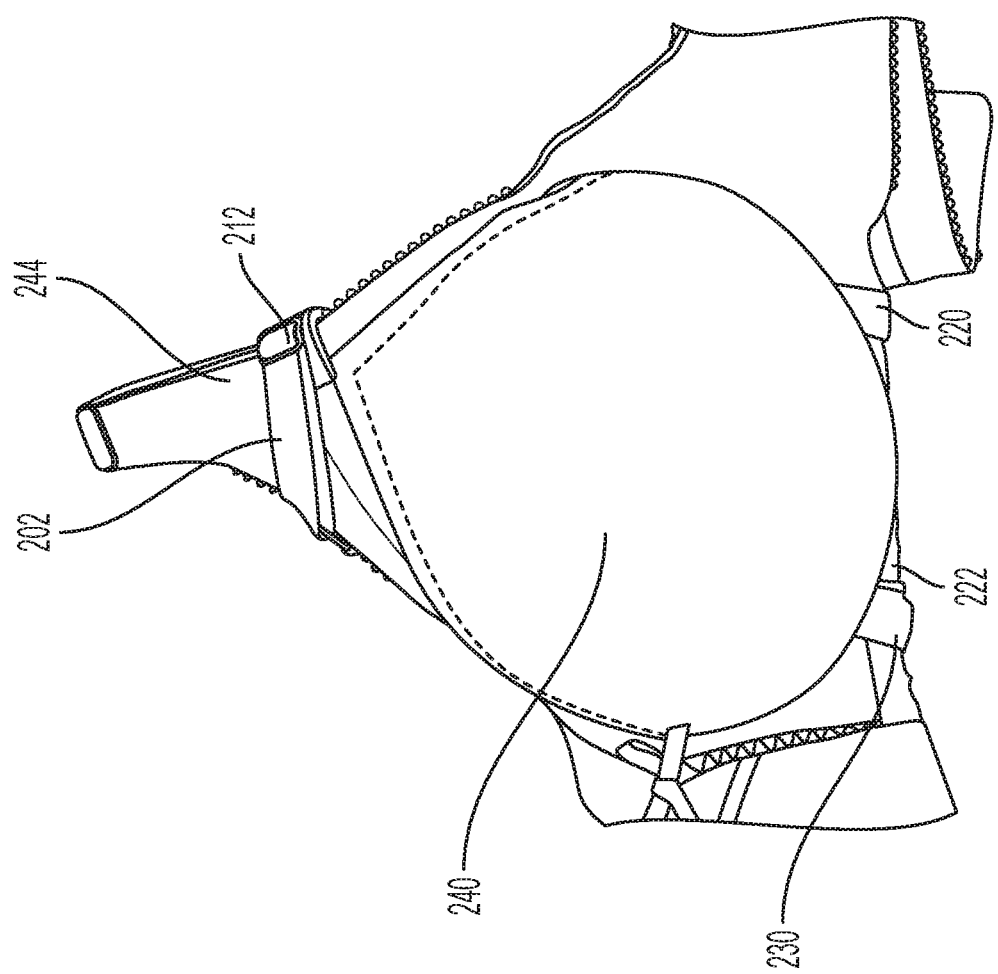
FIG. 6 shows a front view of the prosthesis in fully attached position on the right side of bra.

FIG. 6 shows a front view of the prosthesis in fully attached position on the right side of bra 244. Strap 202 wraps around bra strap 244. Slide 212 is adjusted for a tight fit. Straps 220 and 230 are folded over such that the corresponding magnets attract. Straps are shown over front bra band 222 instead of over the cup, which is possible if the user prefers. The prosthesis body is behind the bra cup, securely attached.

As shown in FIGS. 7A-7D, in some embodiments, the prosthesis body is comprised of several different pieces including the cover 601 and the internal components, which may comprise a shaper 660, insert 670, and in some embodiments, weight strip 680. Note that in some embodiments, not all internal components are present. These components make for easy customization and washing of the various parts of the prosthesis.

Figure 7A:
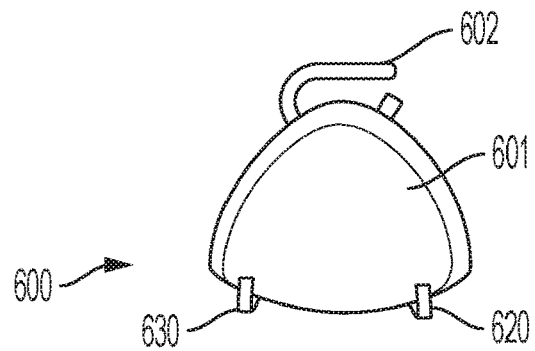
FIG. 7A shows a cover.

FIG. 7A shows cover 601. In some embodiments, the straps 602, 620, and 630 are attached to cover 601. Straps 602, 620, and 630 are similar to straps 102, 120, and 130. Inside the cover fits the internal components.

Figure 7B:
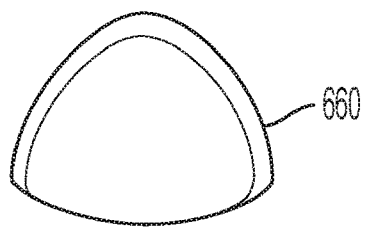
FIG. 7B shows a shaper.

FIG. 7B shows shaper 660. Shaper 660 is shaped like a breast, and in some embodiments, may be made from wool or another suitable material. The shaper 660 has a convex side and a concave side (opposite the concave side) to give a convex shape to the prosthesis when worn with the concave side toward the wearer's body. Shaper 660 is made from a material that is taut to give shape, yet having some softness. Note that the amount of filler can be customized by the user in some embodiments to make insert of preferred volume.

Figure 7C:
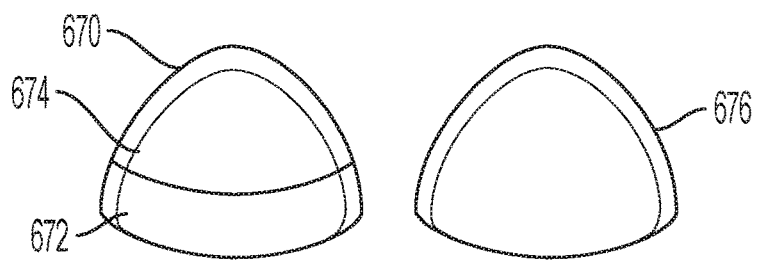
FIG. 7C shows an insert that fits into the convex portion of the shaper.

FIG. 7C shows an insert 670 that fits into the convex portion of the shaper. The insert 670, like a pillow, may have a substantially soft shell and be filled with a soft filler. The filler can serve to create volume. The filler may be cotton, polyester, feathers, a semi-solid gel piece, or other suitable material. The insert 670 may have a pouch (pocket with space between the shell and wall denoted at 672, on a first side 674, which may hold weights. The second side is shown as 676 without a pouch.

Figure 7D:
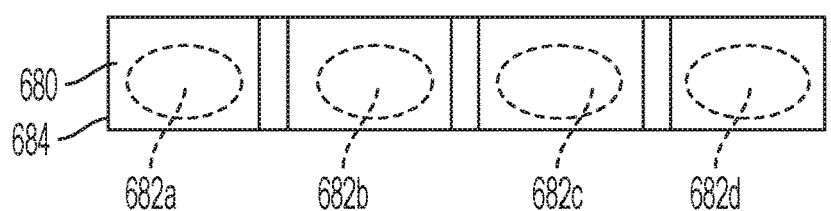
FIG. 7D shows a weight strip.

FIG. 7D shows a weight strip 680. The weights may be connected to one another as a weight strip 680. The amount of the weight may be user adjustable. There may be a plurality of weights 682a, 682b, 682c, and 682d. The weights may be glass mandrels or other suitable material. The weights may be sewn into pockets in a piece of fabric 684 to form the strip 680. The user can cut off some of the pockets holding weights to reduce the amount of weight if they so desire. The amount of weight can be customized such that it matches the weight of another prosthesis in the other cup of the bra, or for comfort if the user has breast material to fill the other side of the bra. Although four weights are shown, in implementations, more or fewer may be included.

Figure 8:
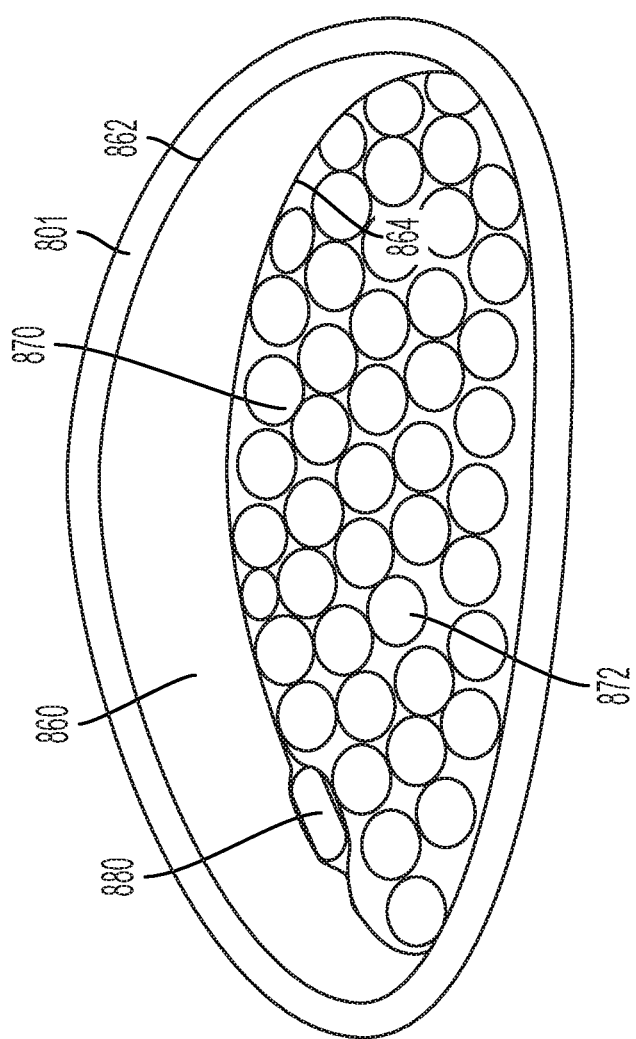
FIG. 8 shows a cross-section diagram of the components of FIG. 7A-7D as they may fit together.

FIG. 8 shows a cross-section diagram of the components of FIG. 7A-7D as they may fit together (straps are omitted for clarity). The cover 801 (similar to 601) is on the outside with hollow interior chamber 820. Therein fits the shaper 860 (similar to 660), under which is the filler 870. The weight strip 880 (similar to 680) wedges between the insert 870 (similar to 670) (filled with filler 872) and the shaper 860 in the insert's pouch. Note that the shaper has a convex side 862 and a concave side 864. Insert 870 fits into the concave side 864 of the shaper 860.

Figure 9A:
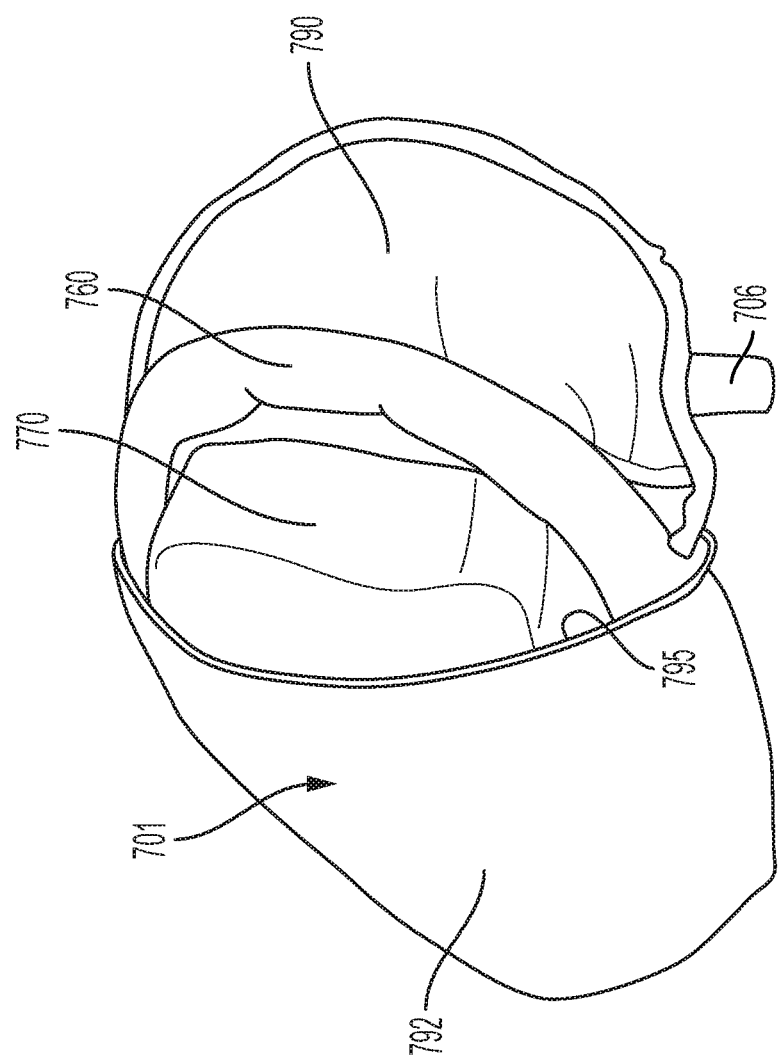
FIG. 9A shows the prosthesis body partially-assembled.
Figure 9B:
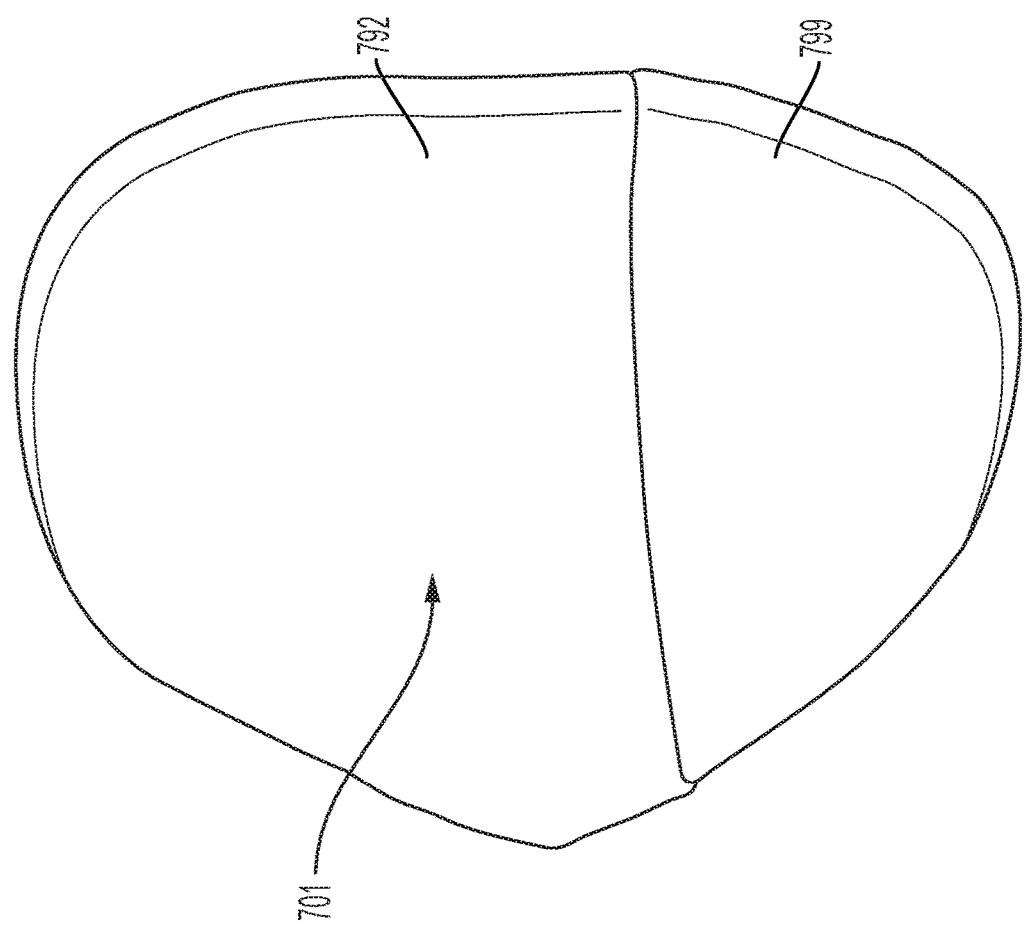
FIG. 9B shows the prosthesis body fully assembled.

FIGS. 9A and 9B show the prosthesis body partially-assembled and fully assembled, respectively. FIG. 9A shows the internal components, including the shaper 760 and the insert 770 (having a filler material therein), partially inside an interior 795 of the cover. The interior is formed by two pocket-like portions. An external side of first pocket-like portion is referenced at 792 of the cover 701. The cover 701 is hollow with an opening 795 for insertion of the internal components. An internal side of second pocket-like portion 790 is pulled inside-out over the internal components. Inner portion of a strap holding a magnet is shown at 706 (representative of inner strap portion 103 or 105). FIG. 9B shows the back side of the cover 701 with internal components therein, fully assembled (FIG. 7A shows example of front side). Instead of it being substantially flat, when the hollow chamber is empty, it is now bulbous with volume to fill in a bra cup like a breast would. The loop and straps are not in view here. The side shown in FIG. 9A has now been turned inside out so that an exterior surface is shown at 799.

Note that shown in FIGS. 9A-9B, there is shown is an example method of assembling the prosthesis body. Other configurations of the hollow cover are included within the scope of the invention, as well as relevant assembly methods.

Figure 10:
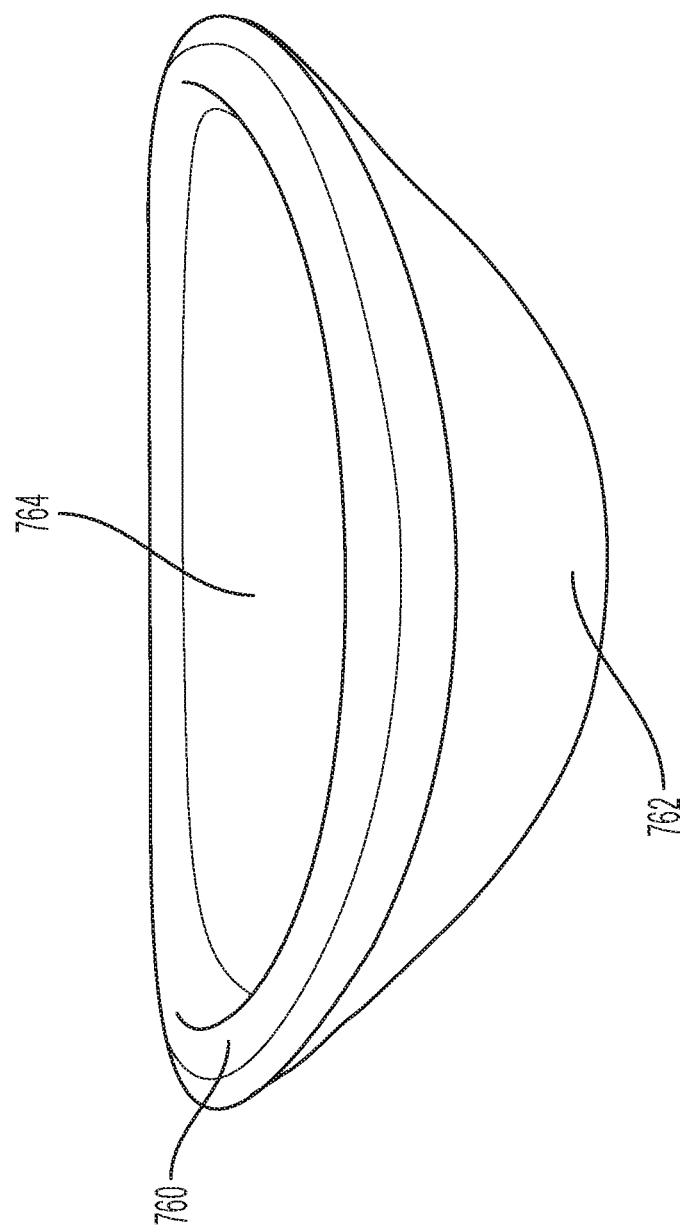
FIG. 10 shows a view of the shaper with the concave side up and convex side facing downward.

FIG. 10 shows a view of the shaper 760 with the concave side 764 up and convex side 762 facing downward.

Figure 11:
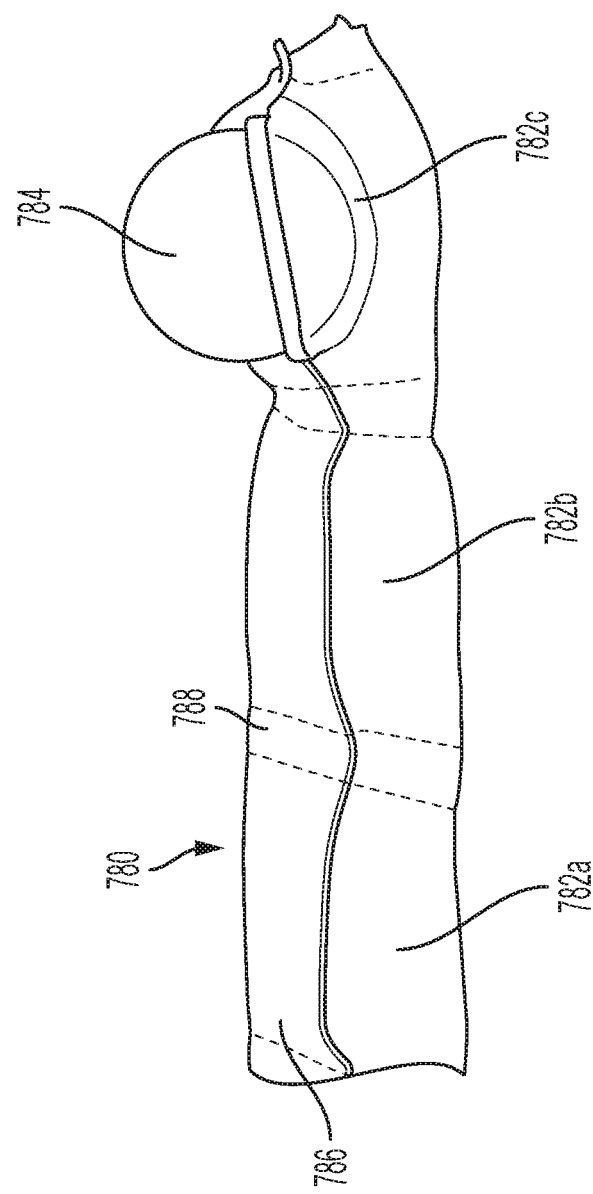
FIG. 11 shows a top-down view of a weight strip.

FIG. 11 shows a top-down view of the weight strip 780. Weight strip 780 has several pockets 782a, 782b, 782c, in which weights can be inserted or removed. Weight 784 is shown partially removed from the interior of pocket 782c. The strip pockets are made of fabric 786 or other suitable material. In between the edges of the pockets is extra material 788, which can be cut by the user if they want to reduce the number of weights. Note that in other embodiments, weights may be included in the prosthesis in another way. In embodiments, the weight strip is a cloth strip. In some embodiments, there are more or fewer of the pockets than the three shown.

FIG. 12 shows a hook 1200 in accordance with embodiments. Hook 108 and 208 in previous figures. Hook 1200 includes closed loop 1250 (for non-removably attaching a strap to the prosthesis body) and open loop 1255 (for removably attaching a strap to a prosthesis body loop (not shown). In some embodiments, the hook is plastic, metal, or other suitable material.

Figure 13A:
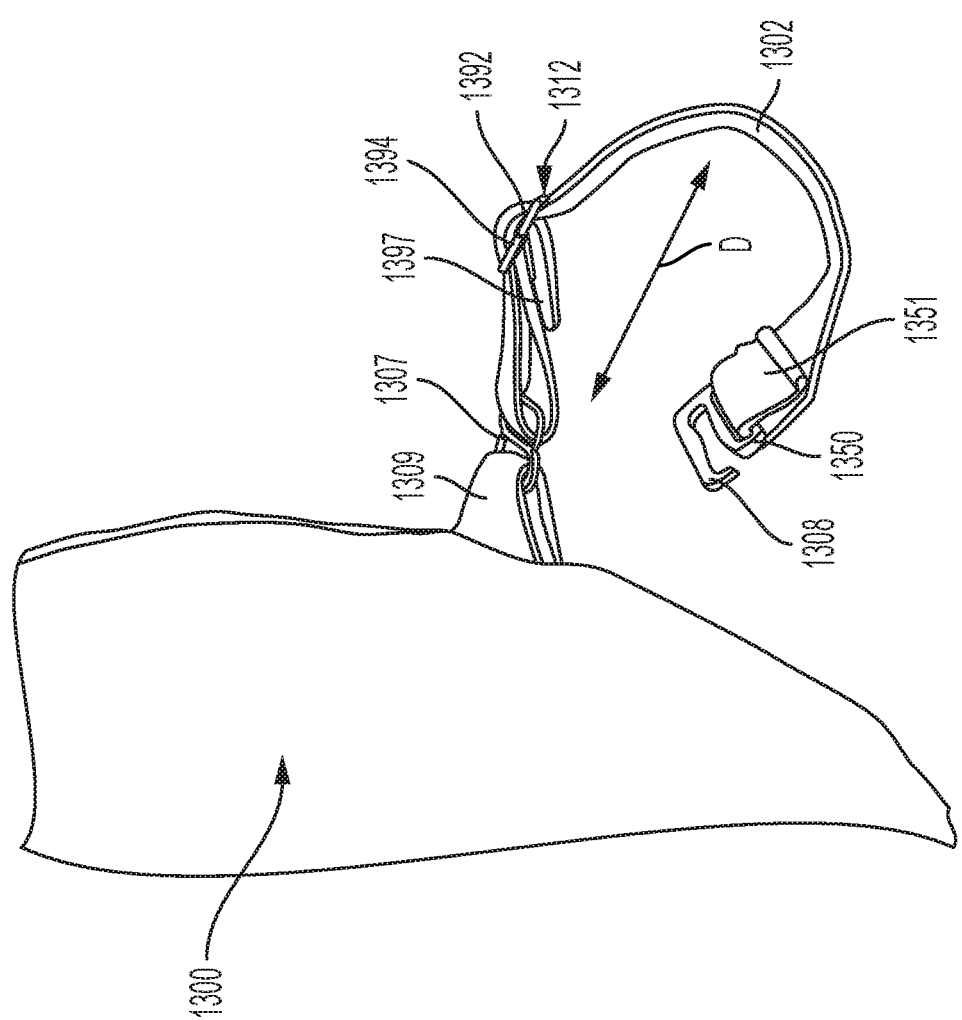
FIG. 13A shows an example adjustable strap.
Figure 13B:
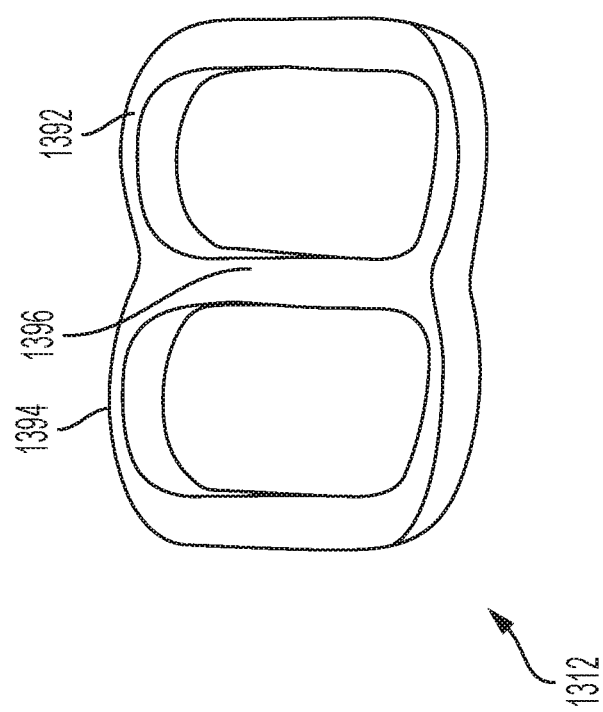
FIG. 13B shows a rendering of a slide.

FIG. 13A shows an example adjustable strap 1302, similar to strap 102 of FIG. 1. In embodiments, the adjustable strap 1302 comprises a woven blend of nylon and spandex. In some specific embodiments, the blend is 90% nylon and 10% spandex. In some embodiments, the adjustable strap 1302 comprises a woven blend of polyester and spandex. In some specific embodiments, the blend is 90% polyester and 10% spandex. FIG. 13B shows a rendering of a slide 1312 (slide 112 and slide 212 of previous figures are similar to slide 1312). Slide 1312 has two closed loops 1392, 1394 with a center bar 1396 running through the middle. In some embodiments, the slide is made from plastic, metal, or other suitable material. Strap 1302 attaches to hook 1308 via wrapping through loop 1350 on the hook 1308, and attaching back to itself at 1351. Strap 1302 threads through loop 1392, over middle bar 1396, and through loop 1394. It threads through a loop on clasp 1307. It threads back through loop 1394 over middle bar 1396 and through loop 1392. It attaches to itself at 1397. Clasp 1307 attaches to prosthesis body loop 1309, which attaches to prosthesis body 1300 (partial view shown). This arrangement allows the slide to be moved, as shown by arrow 1395, by a user so as to adjust the length of the strap 1302. Note that clasp 1307 is similar in structure to slide 1312 (though it could be configured differently in other embodiments).

Figure 14:
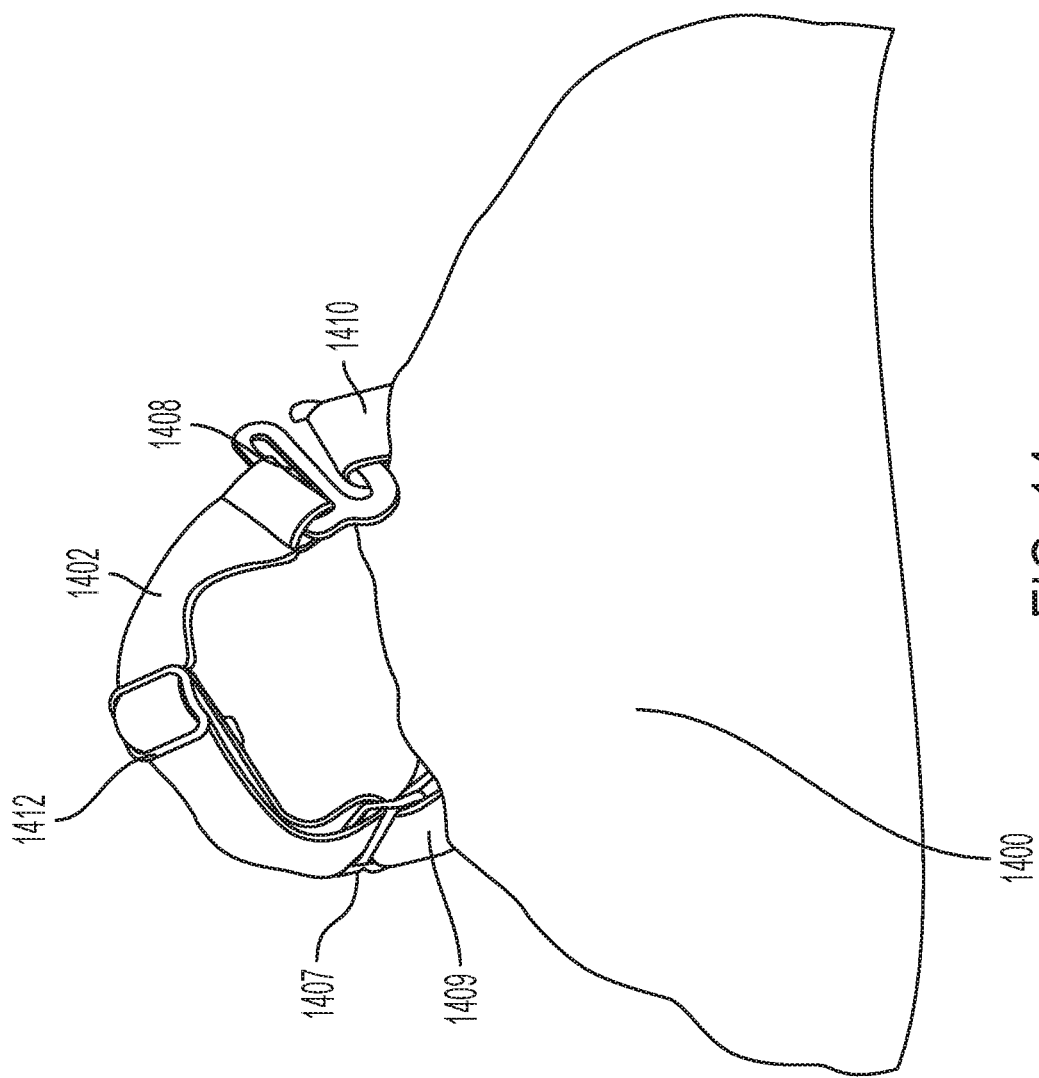
FIG. 14 shows an upper portion of the breast prosthesis assembled.

FIG. 14 shows an upper portion of the breast prosthesis assembled. Strap 1402 is similar to strap 102 of FIG. 1. Body 1400 has loops 1409 and 1410 attached. Strap 1402 is attached to loop 1409 via clasp 1407. Strap 1402 is removably attached to loop 1410 via hook 1408. Strap 1402 is adjustable in length via slide 1412. Cover 1400 is shown in partial view.

In some embodiments, the cover, loops, insert walls, and straps are made from cloth, fabric, spandex, polyester or other suitable material. In some embodiments, the shaper is made from wool or another soft, yet firm/stiff material. In some embodiments, the slide, hooks and clasps are made from metal, plastic, or other suitable material.

In some embodiments, the materials of embodiments are all-natural. In some embodiments, the cover and insert shell are GOTS certified jersey cotton material. The filler inside the shell may be GOTS certified raw cotton batting. The shaper may be made from wool batting or alpaca batting made into a felt material.

Other materials that may be used, in some embodiments, are GOTS Certified Twill Tape, GOTS Certified Thread-natural color, Glass rondels for the adjustable weight system, magnets, and water and cornstarch for embodiments that use an all-natural stiffener for the shaper.

FIG. 15 shows a cross-section of an example 1600 of embodiments of the body having a cover and an alternative filler which is semi-solid. In such embodiments, the cover 1601 is the same as described including the straps, but instead of a shaper, insert, and weights, a semi-solid gel insert 1650 is removably set into the hollow interior of the cover. The insert may be made from silicon, plastic, or other suitable material. The cover is similar to the covers described for embodiments, having straps, loops, magnets, etc.

In alternative embodiments, the cover (having the magnets therein) is filled with items or material other than what is described herein, or in addition to those described herein. For example, the cover could be filled with cotton, silicone pieces, soft plastic, foam, or some other material. In some embodiments, the straps and magnets are attached to a unitary body (which could be silicone or another material).

While the invention has been particularly shown and described in conjunction with exemplary embodiments, it will be appreciated that variations and modifications will occur to those skilled in the art. For example, although some of the illustrative embodiments are described herein as a series of acts or events, it will be appreciated that the present invention is not limited by the illustrated ordering of such acts or events unless specifically stated. Some acts may occur in different orders and/or concurrently with other acts or events apart from those illustrated and/or described herein, in accordance with the invention. In addition, not all illustrated steps may be required to implement a methodology in accordance with the present invention. Furthermore, the methods according to the present invention may be implemented in association with the formation and/or processing of structures illustrated and described herein as well as in association with other structures not illustrated. Moreover, in particular regard to the various functions performed by the above described components (assemblies, devices, circuits, etc.), the terms used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more features of the other embodiments as may be desired and advantageous for any given or particular application. Therefore, it is to be understood that the appended claims are intended to cover all such modifications and changes that fall within the true spirit of the invention.

I claim:
1. A breast prosthesis comprising:
a cover and at least one internal component, wherein the cover has a hollow interior;
a first strap;
an attachment point for the first strap;
a second strap having a first portion that extends from an exterior of the cover,
wherein the first portion of the second strap has a first magnet therein; and
a third strap having a first portion that extends from the exterior of the cover of the prothesis, wherein the first portion of the third strap has a second magnet therein;

wherein the at least one internal component includes a third magnet and a fourth magnet;

wherein the first strap is configured to attach around a bra strap;

wherein the second strap is configured to wrap over a bra cup and attach via the third magnet attracting the first magnet; and wherein the third strap is configured to wrap over the bra cup and attach via the fourth magnet attracting the second magnet.

2. The breast prosthesis of claim 1, wherein the at least one internal component further comprises:
   a shaper, and
   an insert comprising a filler.

3. The breast prosthesis of claim 2, wherein the at least one internal component further comprises at least one weight, wherein the weight can fit within a pouch on the insert.

4. The breast prosthesis of claim 3, wherein the at least one weight is a plurality of weights in pockets of a cloth strip.

5. The breast prosthesis of claim 2, wherein the filler is a soft material that creates volume.

6. The breast prosthesis of claim 2, wherein the shaper has a convex side and a concave side.

7. A breast prosthesis comprising:
   a cover and at least one internal component, wherein the cover has a hollow interior;
   a first strap;
   an attachment point for the first strap;
   a second strap having a first portion that extends from an exterior of the cover,
   wherein the first portion of the second strap has a first magnet therein; and
   a third strap having a first portion that extends from the exterior of the cover of the prothesis, wherein the first portion of the third strap has a second magnet therein; and
   wherein the at least one internal component includes a third magnet and a fourth magnet; and
   wherein the second strap and the third strap each have a second portion that extends into the interior of the body of the prosthesis, and wherein the third magnet is disposed within the second portion of the second strap and the fourth magnet is disposed within the second portion of the third strap.

8. The breast prosthesis of claim 1, wherein the at least one internal component comprises a semi-solid piece.

9. A system comprising:
   a bra, and
   a breast prosthesis, wherein the breast prosthesis comprises:
   a cover and at least one internal component, wherein the cover has a hollow interior;
   a first strap;
   an attachment point for the first strap;
   a second strap having a first portion that extends from an exterior of the cover, wherein the first portion of the second strap has a first magnet therein; and
   a third strap having a first portion that extends from the exterior of the cover of the prothesis, wherein the first portion of the third strap has a second magnet therein;
   wherein the at least one internal component includes a third magnet and a fourth magnet;
   wherein the first strap is configured to attach around a bra strap of the bra;
   wherein the second strap is configured to wrap over a bra cup of the bra and attach via the third magnet attracting the first magnet; and
   wherein the third strap is configured to wrap over the bra cup of the bra and attach via the fourth magnet attracting the second magnet.

10. The system of claim 9, wherein the at least one internal component further comprises:
    a shaper, and
    an insert comprising a filler.

11. The system of claim 10, wherein the at least one internal component further comprises at least one weight, wherein the weight can fit within a pouch on the insert.

12. The system of claim 11, wherein the at least one weight is a plurality of weights in pockets of a cloth strip.

13. The system of claim 10, wherein the filler is a soft material that creates volume.

14. The system of claim 10, wherein the shaper has a convex side and a concave side.

15. The system of claim 9, wherein the second strap and the third strap each have a second portion that extends into the interior of the body of the prosthesis, and wherein the third magnet is disposed within the second portion of the second strap and the fourth magnet is disposed within the second portion of the third strap.

16. The breast prosthesis of claim 7, wherein the at least one internal component comprises a semi-solid piece.

17. The breast prosthesis of claim 7, wherein the at least one internal component further comprises:
    a shaper, and
    an insert comprising a filler.

18. The breast prosthesis of claim 17, wherein the filler is a soft material that creates volume.

19. The breast prosthesis of claim 17, wherein the shaper has a convex side and a concave side.

* * * * *